United States Patent

Hahnen

[11] Patent Number: 5,938,661
[45] Date of Patent: Aug. 17, 1999

[54] SINGLE ARM ELECTROCAUTERY PROBES FOR USE WITH A RESECTOSCOPE

[75] Inventor: Kevin F. Hahnen, Pleasanton, Calif.

[73] Assignee: Symbosis Corporation, Miami, Fla.

[21] Appl. No.: 08/795,000

[22] Filed: Feb. 5, 1997

[51] Int. Cl.⁶ .................................................. A61B 17/39
[52] U.S. Cl. ........................... 606/46; 606/49; 607/147
[58] Field of Search .................................. 606/45, 46, 49; 601/19; 607/147

[56] References Cited

U.S. PATENT DOCUMENTS

| | | | |
|---|---|---|---|
| 1,930,214 | 10/1933 | Wappler | 174/89 |
| 1,963,636 | 6/1934 | Wappler | 174/59 |
| 1,971,024 | 8/1934 | Wappler | 174/89 |
| 2,002,594 | 5/1935 | Wappler et al. | 174/89 |
| 2,004,559 | 6/1935 | Wappler et al. | 174/89 |
| 2,011,169 | 8/1935 | Wappler | 174/89 |
| 2,090,923 | 8/1937 | Wappler | 128/303.15 |
| 2,224,464 | 12/1940 | Wolf | 128/303.14 |
| 2,487,502 | 11/1949 | Willinsky | 128/303.14 |
| 2,815,757 | 12/1957 | Piar | 128/303.14 |
| 3,149,633 | 9/1964 | Zingale | 128/303.5 |
| 3,752,159 | 8/1973 | Wappler | 128/303.15 |
| 3,856,015 | 12/1974 | Iglesias | 128/303.15 |
| 3,939,839 | 2/1976 | Curtiss | 128/303.15 |
| 3,973,568 | 8/1976 | Iglesias | 128/303.15 |
| 3,990,456 | 11/1976 | Iglesias | 128/303.15 |
| 4,030,502 | 6/1977 | Iglesias | 128/303.15 |
| 4,134,406 | 1/1979 | Iglesias | 128/303.15 |
| 4,149,538 | 4/1979 | Mrava et al. | 128/303.15 |
| 4,362,160 | 12/1982 | Hiltebrandt | 128/303.15 |
| 4,506,668 | 3/1985 | König | 128/303.15 |
| 4,649,917 | 3/1987 | Karasawa | 128/303.14 |
| 4,657,018 | 4/1987 | Hakky | 128/303.15 |
| 4,726,370 | 2/1988 | Karasawa et al. | 128/303.15 |
| 4,917,082 | 4/1990 | Grossi et al. | 606/46 |
| 5,007,907 | 4/1991 | Nishigaki et al. | 606/46 |
| 5,064,424 | 11/1991 | Bitrolf | 606/46 |
| 5,088,998 | 2/1992 | Sakashita et al. | 606/46 |
| 5,196,011 | 3/1993 | Korth et al. | 606/46 |
| 5,201,741 | 4/1993 | Dulebohn | 606/113 |
| 5,261,906 | 11/1993 | Pennino et al. | 606/45 |
| 5,318,564 | 6/1994 | Eggers | 606/47 |
| 5,324,288 | 6/1994 | Billings et al. | 606/45 |
| 5,342,357 | 8/1994 | Nardella | 606/40 |
| 5,354,296 | 10/1994 | Turkel | 606/41 |
| 5,374,188 | 12/1994 | Frank et al. | 433/32 |
| 5,376,087 | 12/1994 | Haber et al. | 606/27 |
| 5,395,312 | 3/1995 | Desai | 604/22 |
| 5,395,363 | 3/1995 | Billings et al. | 606/50 |
| 5,395,368 | 3/1995 | Ellman et al. | 606/45 |
| 5,582,610 | 12/1996 | Grossi et al. | 606/46 |
| 5,599,349 | 2/1997 | D'Amelio | 606/46 |

FOREIGN PATENT DOCUMENTS

| | | | |
|---|---|---|---|
| 3707-403 | 9/1987 | Germany | 606/46 |
| 26880 | 12/1906 | United Kingdom | 601/19 |

*Primary Examiner*—Lee Cohen
*Attorney, Agent, or Firm*—Testa, Hurwitz & Thibeault, LLP

[57] ABSTRACT

An electrocautery probe includes a single probe arm and an electrode. The electrode includes one end attached to the probe arm and a free end. According to one embodiment of the invention, the electrode is a wedge, preferably having a substantially triangular cross section. According to another embodiment of the invention, the free end of the electrode rises higher than the attached end of the electrode. The free end of the electrode may be planar, pointed, or rounded. Where the free end of the electrode is planar, it may be inclined in either the proximal or distal direction. According to yet another embodiment of the invention, the electrode is a roller barrel. The electrocautery probe has several advantages over two armed electrocautery probes. First, the electrocautery probe has only one arm obscuring the physician's view through the lens of the resectoscope. Second, the free end of the electrode can be used for sculpting tissue and for resecting tissue in narrow areas. Third, the free end of the electrode can be used for spot coagulation. Fourth, the free end is capable of larger resections than possible with a two-armed electrocautery probe. In addition, the electrocautery probe fits into a standard resectoscope without modification to the resectoscope device.

18 Claims, 4 Drawing Sheets

SINGLE ARM ELECTROCAUTERY PROBES FOR USE WITH A RESECTOSCOPE

This application is related to U.S. Pat. No. 5,569,244, and is also related to U.S. Ser. No. 08/425,363 filed Apr. 20, 1995, now U.S. Pat. No. 5,779,700, the complete disclosures of which are hereby incorporated in their entireties herein by reference.

BACKGROUND OF THE INVENTION

1. Field of the Invention

This invention relates broadly to endoscopic instruments. More particularly, this invention relates to electrocautery probes for use with a resectoscope.

2. State of the Art

Electrosurgical resection is a procedure in which damaged or enlarged tissue is excised with an electrocautery probe. Transurethral resection is an electrosurgical procedure in which a portion of the prostrate is excised by means of an instrument passed through the urethra. Endometrial ablation is an electrosurgical alternative procedure to hysterectomy for women with menorrhagia (abnormal or excessive uterine bleeding). In both procedures, the instrument typically used is called a resectoscope or hysteroscope. Prior art FIG. 1 shows a typical resectoscope 10 with an electrocautery probe 12. The resectoscope 10 includes a distal guide tube 14 and a body 16 having a stationary handle portion 17 and a movable handle portion 19. A scope 18 is inserted through the guide tube 14 and is provided with a proximal eye piece 20 for viewing the interior of the bladder or other operative site. The scope has a longitudinal axis L. The cautery probe 12 has a distal electrode 22 which is mounted between a pair of arms 23, 25 and is situated in front of the scope 18. The arms 23, 25 extend proximally on either side of the scope and angle downward to be joined at their proximal ends to an electrode lead 27 situated beneath the scope. The electrode lead 27 slidably extends through the housing where at its proximal end the electrode lead is coupled to a wire 24 which is further coupled to a source of cautery current (not shown). A mounting sleeve 29 is provided on the probe 12 for slideably coupling it to the guide tube 14. The mounting sleeve 29 is typically located at the point where the arms 23, 25 are joined to the electrode lead 27. The stationary and movable handle portions 17, 19 are generally capable of axially sliding the probe 12 and its distally mounted electrode 22 relative to the guide tube 14.

The resection procedure involves applying a cauterizing current to the electrode 22 and moving the electrode slowly through or over the prostate or endometrium while viewing the tissue through the scope 18. Thermal energy is applied through the electrode to the prostate or the endometrium so that tissue is excised. The resectoscope and cautery probe are also useful in other procedures for resecting the uterus, ureter, or renal pelvis.

Known electrodes for use in resectoscopes are available in many different shapes and sizes. U.S. Pat. No. 4,917,082 to Grossi et al., for example, discloses several embodiments of a resectoscope electrode including a coagulating electrode, a knife electrode, a punctate electrode, and a roller electrode, among others. Electrodes for use with resectoscopes are also widely available from Olsen Electrosurgical, Inc., Concord, Calif. They are available as blades, needles, balls, loops, spear tips, flexible wires, semi-circular wires, hooks, spatulas and blunt tips.

While differently shaped electrodes are utilized for various different procedures, electrodes of a given shape have a useful surface area limited by the space between the two arms on which they are mounted, and the space between the two arms is limited by the openings through which the instrument is inserted to reach the surgical site. A small surface area, however, compromises the effectiveness of the electrode as a coagulating tool. Thus, in a prostatic resection procedure, it is not uncommon that 80% of the time devoted to the procedure is used to coagulate the prostate and stop it from bleeding. In addition, in many procedures it would be desirable if a single electrode could be sufficiently versatile so as to adequately perform resection, general coagulation, spot coagulation, and tissue sculpting. However, known electrodes are not so versatile, and often multiple electrodes must be used in a single procedure to perform the different functions.

Another difficulty encountered in procedures utilizing electrocautery probes is when the electrocautery probe is moved distally relative to the scope, the arms of the probe tend to occlude the view of the physician through the lens of the scope of the areas lateral of the arms and the electrode. However, procedures utilizing a resectoscope are often involved in resecting and coagulating very delicate tissues in the narrow confines of the urinary and reproductive tracts, and the lower alimentary canal. Therefore, it is important for the physician to have, as much as possible, an unobstructed view through the scope.

One conceivable manner of reducing view obstruction, which is the subject of this invention as disclosed in great detail hereinafter, is to utilize an electrocautery cautery probe having only a single arm to thereby provide greater visibility to the surrounding tissue and to the points of contact between the electrode and the tissue. While the prior art literature does include a few probes having a single arm, it would appear that no commercial devices have incorporated these designs because the designs of the literature include substantial drawbacks. In particular, the single arm probes of the prior art have restricted use and are not at all versatile. For example, U.S. Pat. No. 5,007,907 to Nishigaki et al. discloses an electrocautery probe with a single probe arm having a centrally mounted full loop electrode. The probe arm extends along the top of the scope and does not join an electrode lead, but rather is provided with a female threaded portion for electrically coupling to a male threaded portion of an electrode driving shaft. This unconventional configuration diminishes the desirability of the probe, as typical resectoscopes are adapted for slidably receiving an electrode lead beneath the scope and resectoscopes are not provided with driving shafts having threaded couplings. Therefore, the single armed electrocautery probe of Nishigaki et al. cannot be used with standard resectoscopes.

U.S. Pat. No. 5,196,011 to Korth et al. ostensibly also shows an electrocautery probe with a single arm having a triangular-shaped full loop electrode centrally mounted on the arm and also having a depth gauge coupled to the arm. However, no connection is shown between the probe arm and the resectoscope. Therefore, one can speculate that the probe arm is arguably side mounted, as shown with respect to the multiple arm embodiments in Korth et al., or is top or bottom mounted with no enablement being provided for those possibilities. If the electrocautery probe is intended to be side mounted on the resectoscope, the electrode, being centrally mounted on the probe, would be located substantially off center from the scope, and, as a consequence, a lateral portion of the electrode would be out of view of the physician. Such an electrocautery probe would be dangerous to use because, as stated above, the physician requires a clear view of the tissue coming into contact with the electrode. If the electrocautery probe is intended to be top mounted, i.e., in vertical alignment with a longitudinal axis of the scope, the probe would not be usable with standard resectoscopes. If the electrocautery probe is intended to be bottom mounted in alignment with a longitudinal axis of the scope of the instrument, the electrode would extend too low, out of the view of the physician. As a result, utilization of the non-enabled single arm embodiment of Korth et al. is problematic regardless of how mounted.

SUMMARY OF THE INVENTION

It is therefore an object of the invention to provide a versatile electrocautery probe having an electrode adapted for tissue resection and tissue sculpting.

It is also an object of the invention to provide a versatile electrocautery probe having an electrode adapted for use for coagulation and spot coagulation.

It is another object of the invention to provide an electrocautery probe having an electrode having a relatively larger useful surface area than prior art electrodes of the similar size and shape.

It is a further object of the invention to provide an electrocautery probe which enables a physician to have relatively greater visibility of the surgical site.

In accord with these objects which will be discussed in detail below, the electrocautery probe of the present invention is provided with a single probe arm having an electrode. The electrode includes one end attached to or adjacent to the probe arm and a free end. According to a preferred embodiment of the invention, the electrode is a loop electrode, preferably having a substantially triangular cross section. According to the preferred embodiment, the loop extends downward from the probe arm and then loops upward with the free end of the loop extending higher than the horizontal plane through the probe arm. According to another embodiment of the invention, the electrode is a roller barrel electrode supported by the single probe arm. Regardless of whether the electrode is a loop or roller barrel, the free end of the electrode may be planar, pointed, or rounded. Where the free end of the electrode is planar, it may be inclined in a lateral, proximal, or distal direction. The electrocautery probe is preferably adapted to fit into a standard resectoscope without modification of the resectoscope.

It will be appreciated that the electrode can be used for both cautery cutting and coagulation in the same manner as a typical electrode. It will also be appreciated that the electrocautery probe includes additional features and substantial advantages over electrocautery probes having two arms. First, with only one arm, the electrocautery probe does not interfere much with the physician's view through the lens of the resectoscope, and thereby provides a clearer view to cautery site. Second, with a free end the electrode of the invention has an increased usable surface area, and is able to resect and coagulate along the entire length of the electrode including at the free end. Third, the free end of the electrode can be used for spot coagulation by rotating the electrode so that only the free end is touching the tissue. Fourth, the free end of the electrode can be used for tissue sculpting and for resecting tissue in narrow areas; i.e., tissue in the area of bladder neck and the verumontanum.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
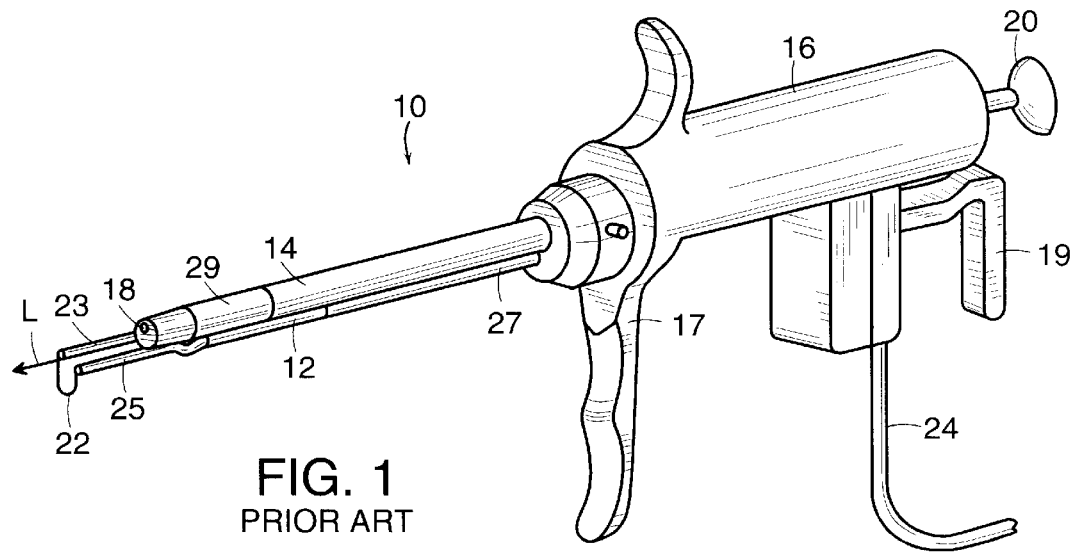
FIG. 1 is a perspective view of a prior art resectoscope with an electrocautery probe having a loop electrode.
Figure 2:
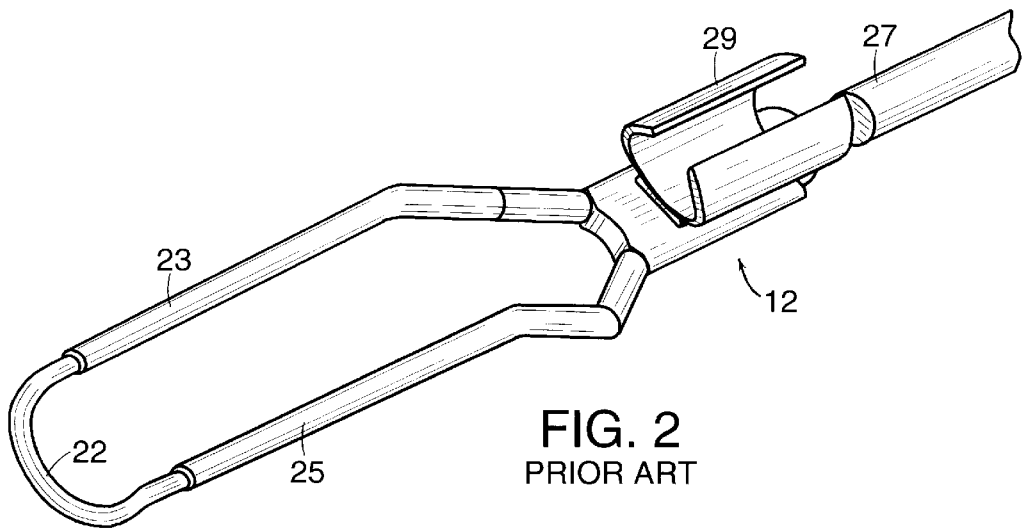
FIG. 2 is an enlarged broken perspective view of the prior art electrocautery probe of FIG. 1.
Figure 3:
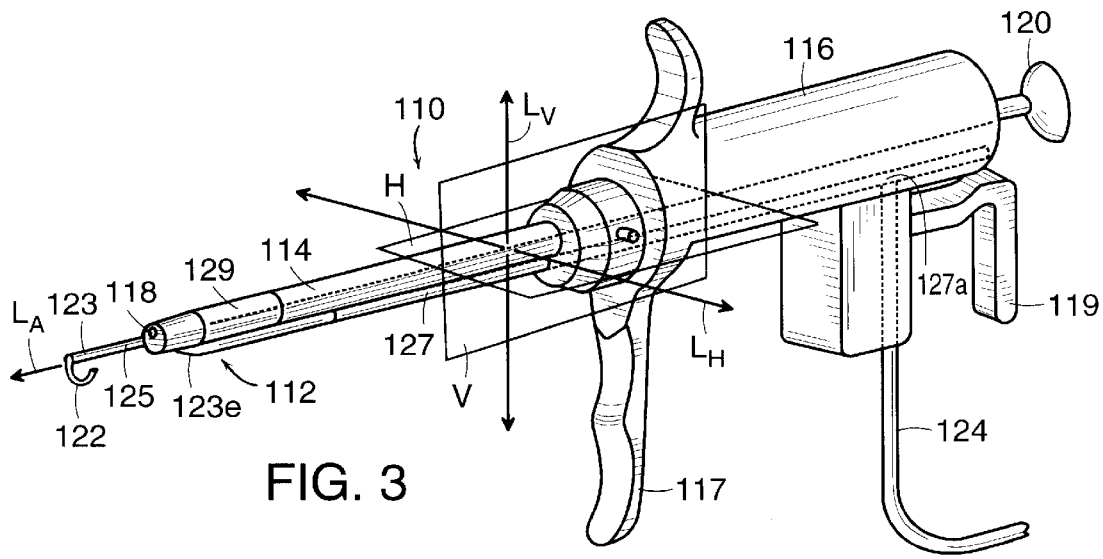
FIG. 3 is a perspective view of resectoscope with an electrocautery probe according to a first embodiment of the invention.

Referring now to FIG. 3, a resectoscope 110 is provided with an electrocautery probe 112 according to the invention. The electrocautery probe 112 has an electrode 122 mounted at the distal end of a conductive probe arm 123. The probe arm is preferably covered in an insulating material 125, such as PTFE. The probe arm 123 is joined at its proximal end to an elongate electrode lead 127, and a resectoscope mounting sleeve 129 coupled to the probe arm is provided preferably at the location where the probe arm 123 is joined to the electrode lead 127. The probe 112 is coupled to a guide tube 114 of the resectoscope 110 at the mounting sleeve 129. The electrode lead 127 extends under the guide tube 114 and slidably further extends through a housing 116 of the resectoscope. The electrode lead 127 is covered in an insulative sheath, and has an exposed proximal end 127a for connection to a wire 124 which is coupled to a cautery supply (not shown). The probe arm 123 includes an upward bend 123a such that a distal portion of the probe arm extends substantially along the guide tube 114. A scope 118 extends through the guide tube 114, which has at its proximal end an eyepiece 120 through which to look through the scope. The housing 116 includes a stationary handle 117 and a movable handle 119 for moving the scope 118 and the probe 112 proximally and distally relative to the stationary handle 117.

Still referring to FIG. 3, several planes are defined for reference: a vertical plane V passes through line $L_V$ and the longitudinal axis $L_A$ of the scope, and a horizontal plane H passes through line $L_H$ and the longitudinal axis $L_A$ of the scope. It will be appreciated that the horizontal and vertical planes shall remain as defined with respect to $L_H$, $L_V$, and $L_A$ regardless of the whether the resectoscope is rotated into an orientation different from the one shown in FIG. 3. Therefore, for purposes herein, all described horizontal planes are parallel to the horizontal plane H and all described vertical planes are parallel to the vertical plane V, and are not restricted to common definitions. It will be appreciated that in a typical resectoscope, the stationary handle 117 is bisected by the vertical plane V.

Figure 4:
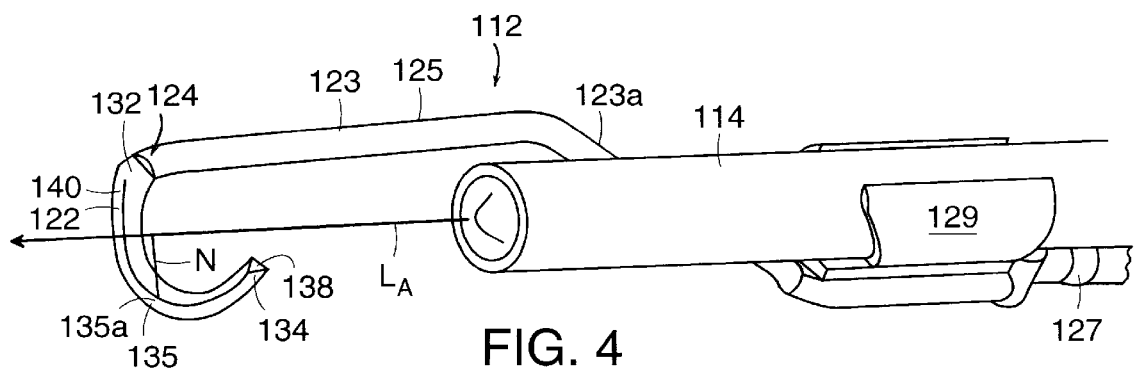
FIG. 4 is an enlarged broken perspective view of the distal end of the electrocautery probe of FIG. 3.
Figure 5:
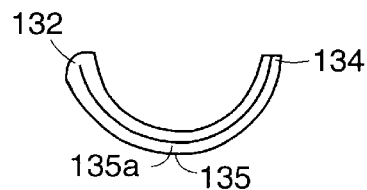
FIG. 5 is an enlarged broken front view of the electrode of the electrocautery probe of FIG. 3.

Referring to FIGS. 3, 4, and 5, according to a first embodiment of the invention, the electrode 122 is a loop electrode. The electrode 122 includes an attached end 132 coupled to the distal end 124 of the probe arm 123, and a free end 134. The electrode 122 loops downward from the attached end 132 to a lowest portion 135 and then loops upwards to the free end 134. The free end 134 preferably lies in substantially the same horizontal plane H as the attached end 132. The electrode 122 is preferably oriented in an orthogonal manner to the distal end 124 of the probe arm 123; i.e., preferably all of the electrode is seen through the scope. The electrode 122 is preferably sized, shaped, and situated such that the lowest portion 135 of the electrode is at the lateral midpoint 135a of the electrode and such that the electrode is substantially aligned with the longitudinal axis $L_A$ of the scope 114; i.e., a line N vertically normal to the longitudinal axis $L_A$ will intersect the electrode 122 at approximately the lateral midpoint 135a. It will be understood that the lowest portion 135 may also be situated, if desired, at a position other than at the lateral midpoint 135a of the electrode 122. The electrode 122 is preferably formed from a bent and shaped portion 140 of the probe arm 123 adjacent the distal end 124, but may also be formed of a separate piece of metal and attached to the distal end 124 of the probe arm 123, for example by welding. The distal end 124 of the probe arm 123 does not intersect the vertical plane V.

Figure 6:
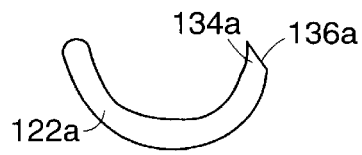
FIG. 6 is an enlarged broken front view of a second embodiment of an electrode for an electrocautery probe according to the invention.
Figure 7:
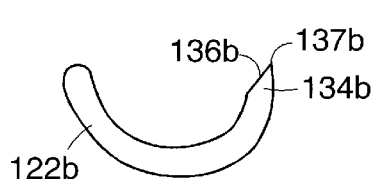
FIG. 7 is an enlarged broken front view of a third embodiment of an electrode for an electrocautery probe according to the invention.
Figure 8:
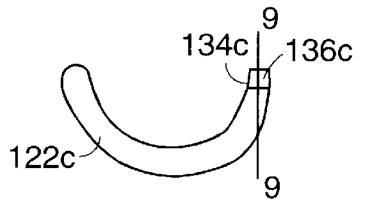
FIG. 8 is an enlarged broken front view of a fourth embodiment of an electrode for an electrocautery probe according to the invention.
Figure 9:
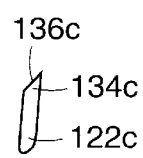
FIG. 9 is a cross-section across line 9—9 in FIG. 8.
Figure 10:
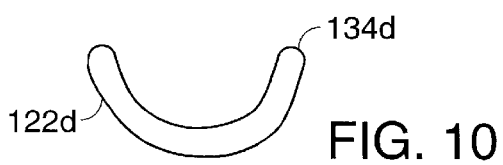
FIG. 10 is an enlarged broken front view of a fifth embodiment of an electrode for an electrocautery probe according to the invention.

The electrode 122 preferably includes a substantially triangular cross-section along a majority of its length, as shown at 138 and described in detail in co-owned U.S. Ser. No. 08/425,386, previously incorporated by reference herein. The free end 134 of the electrode 122 is preferably planar, and may be inclined in a lateral, proximal or distal direction relative to the arm 123. Referring to FIG. 5, the free end 134 is shown horizontally planar. With reference to FIGS. 6 through 10 other exemplary embodiments of the electrode are shown. In FIG. 6, the electrode 122a has a free end 134a inwardly inclined, thereby resulting in a lateral surface 136b. In FIG. 7, the electrode 122b has a free end 134b having an inwardly inclined surface 136b, and a peripheral, preferably knife-sharp, edge 137b. In FIGS. 8 and 9, the electrode 122c includes a free end 134c which is distally inclined, resulting in a distal surface 136c. In FIG. 10, the free end 134d of the electrode 122d is rounded.

It will be appreciated that in each of the embodiments the electrode can be used for both cautery cutting and coagulation in the same manner as a typical electrode. It will also be appreciated that the electrocautery probe includes additional features and substantial advantage over electrocautery probes of the prior art which include two arms. First, with only one arm, the electrocautery probe does not interfere much with the physician's view through the lens of the resectoscope, and thereby provides a clearer view to cautery site. Second, with a free end the electrode of the invention has an increased usable surface area, and is able to cauterize and coagulate along the entire length of the electrode including at the free end. Third, the free end of the electrode can be used for spot coagulation by rotating the electrode so that only the free end is touching the tissue. Fourth, the free end of the electrode can be used for tissue sculpting and for resecting tissue in narrow areas; i.e., tissue in the area of bladder neck and the verumontanum.

Figure 11:
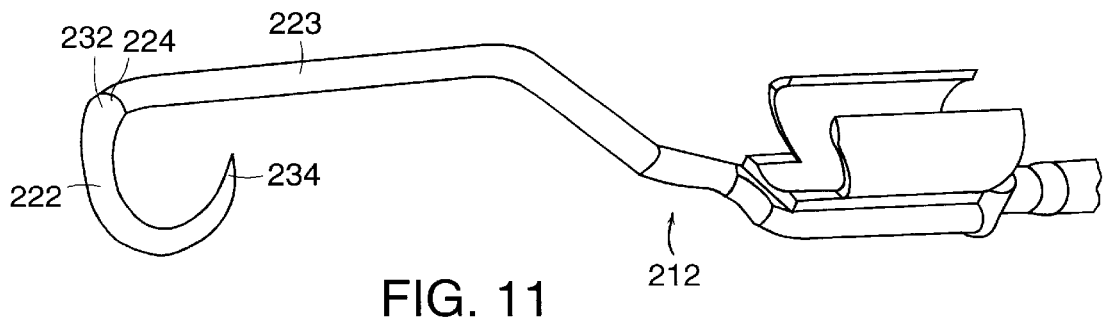
FIG. 11 is an enlarged broken perspective view of the distal end of an electrocautery probe according to a sixth embodiment of the invention.
Figure 12:
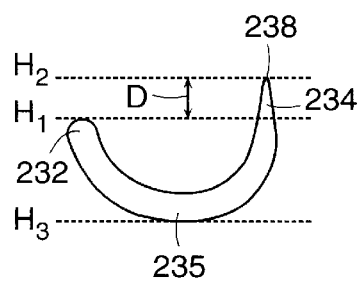
FIG. 12 is an enlarged broken front view of the electrode of the electrocautery probe shown in FIG. 11.

Turning now to FIGS. 11 and 12, a preferred embodiment of an electrocautery probe 212, substantially similar to the first embodiment of the invention, is shown. The electrocautery probe 212 includes a probe arm 223 having an electrode 222 coupled thereto. The electrode 222 has an attached end 232 coupled to the distal 224 end of the probe arm 223, and a free end 234. The electrode 222 loops downward from the attached end 232 to a lowermost portion 235 and then back up to terminate in the free end 234 which extends a distance D higher than the attached end 232. The distance D is typically 0.10 inches, but may be longer or shorter. As such, the attached end 232 is located in a horizontal plane $H_1$ which is situated between a horizontal plane $H_2$ passing through the free end 234 and a horizontal plane $H_3$ passing through the lowermost portion 235, wherein each of the horizontal planes $H_1$, $H_2$, and $H_3$ are parallel to the horizontal plane H shown in FIG. 3. Preferably the free end 234 terminates in a pointed tip 238, but may be rounded or planar, as described above.

It will be appreciated that the extension of the free end 234 beyond the horizontal plane $H_1$, of the attached end 232 allows the free end 234 of the electrode to resect in narrow areas. It will also be appreciated that the pointed tip 238 of the electrode 222 provides enhanced ability to sculpt and resect tissue in exacting procedures. Furthermore, the use of a single arm and the extension of the free end enable larger and deeper resections.

Figure 13:
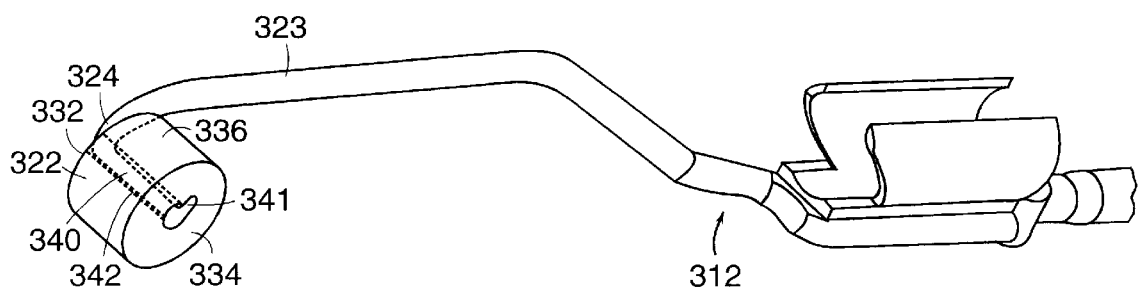
FIG. 13 is an enlarged broken perspective view of the distal end of an electrocautery probe according to a seventh embodiment of the invention.
Figure 14:
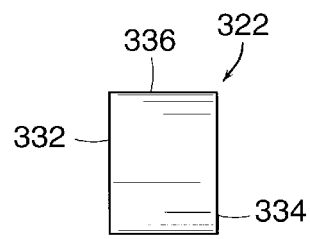
FIG. 14 is an enlarged front view of the electrode of the electrocautery probe shown in FIG. 13.

Referring to FIGS. 13 and 14, another embodiment of an electrocautery probe 312, substantially similar to the first embodiment of the invention, is shown. The electrocautery probe 312 includes a roller bar electrode 322 approximately 2.5 mm long and having a central bore 342. The electrode 322 is preferably rotatably mounted on a bent axle portion 340 of the probe arm 323 extending through the central bore 342, and retained on the bent axle portion 340 by enlarging and/or bending the end 341 of the bent axle portion. The electrode may also be mounted on a conductive axle (not shown) coupled to the distal end 324 of the arm 323, for example, by welding. The electrode 322 is mounted such that substantially all of the electrode is visible through the scope. The electrode has a first end 332 adjacent the distal end 324 of the probe arm 323 (also referred to as "attached" to the distal end 324, even though the roller bar is rotatably mounted), a free end 334, and a circumferential outer surface 336. The outer surface 336 of the electrode 322 may be smooth or may be provided with a plurality of grooves, as described in previously incorporated U.S. Ser. No. 08/425,363. The free end 334 is preferably substantially planar and orthogonal to the outer surface 336.

It will be appreciated that the free end 334 of the roller bar electrode 322 provides an approximately fifty percent or greater increase in the surface area usable for tissue vaporization and coagulation and further permits the electrode to vaporize and coagulate in three planes orthogonal to each other: a substantially horizontal plane (parallel to the horizontal plane H shown in FIG. 3) under or over the roller, a substantially vertical plane parallel to the surface of the free end 334 of the roller bar electrode 322 (and parallel to the vertical plane V shown in FIG. 3), and a vertical plane in front of the roller (orthogonal to both the vertical and horizontal planes, V and H).

Figure 15:
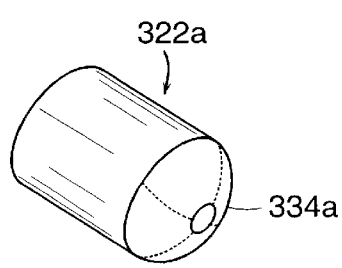
FIG. 15 is a perspective view of an eighth embodiment of an electrode for an electrocautery probe according to the invention.
Figure 16:
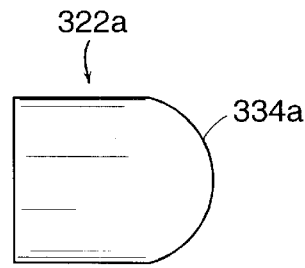
FIG. 16 is an enlarged front view of the electrode shown in FIG. 15.
Figure 17:
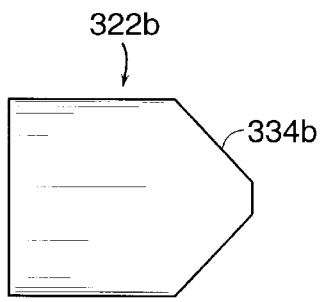
FIG. 17 is an enlarged front view of a ninth embodiment of an electrode for an electrocautery probe according to the invention.
Figure 18:
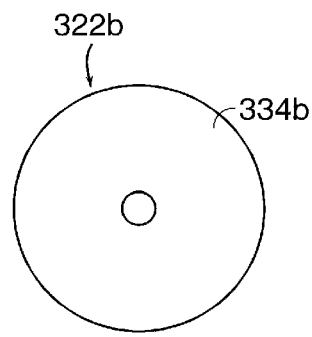
FIG. 18 is an side elevational view of the electrode shown in FIG. 17.

Referring to FIGS. 15 through 18, other embodiments of a roller bar electrode are shown. As seen in FIGS. 15 and 16, the free end 334a of the electrode 322a may be substantially rounded, and, as such, the free end is provided with an increased surface area for coagulation. As seen in FIGS. 17 and 18, the free end 334b of the electrode 322b may be substantially conical. The conical free end 334b may be used for coagulation along a majority of its surface, and for spot coagulation at the vertex of the free end.

Figure 19:
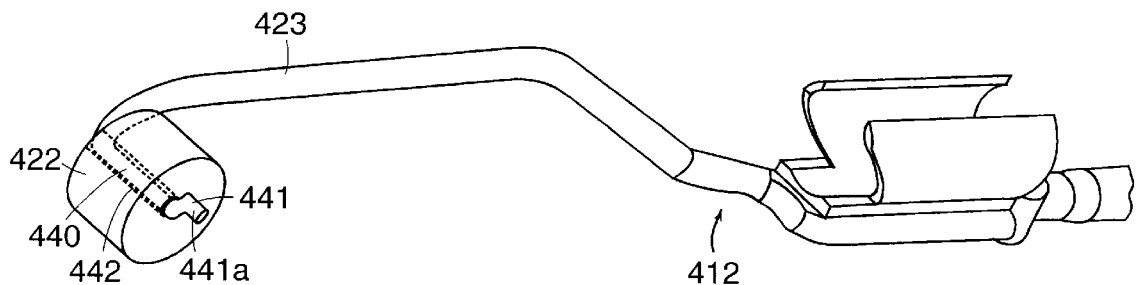
FIG. 19 is an enlarged broken perspective view of the distal end of an electrocautery probe according to a tenth embodiment of the invention.

Turning to FIG. 19, another embodiment of an electrocautery probe 412, substantially similar to the first embodiment of the invention, is shown. The electrocautery probe 412 includes a roller bar electrode 422 having a central bore 442. The electrode 422 is preferably rotatably mounted on a bent axle portion 440 of the probe arm 423 extending through the central bore 442. The bent axle portion 440 has a Z-bend 441 which retains the electrode 422 on the bent axle portion, and an extended end 441a. The extended end 441a is relatively small in diameter but may be further sharpened to a point. The extended end 441a of the bent axle portion 440 may be used for spot coagulation and tissue sculpting.

There have been described and illustrated herein several embodiments of an electrocautery probe for use in a resectoscope. While particular embodiments of the invention have been described, it is not intended that the invention be limited thereto, as it is intended that the invention be as broad in scope as the art will allow and that the specification be read likewise. Thus, while particular configurations have been disclosed with regard to electrodes for the electrocautery probe, it will be appreciated that electrodes otherwise shaped, sized, and oriented could be utilized with the single arm electrocautery probe of the invention. It will therefore be appreciated by those skilled in the art that yet other modifications could be made to the provided invention without deviating from its spirit and scope as so claimed.

I claim:

1. An electrosurgical device, comprising:
   a) an electrocautery probe comprising exactly one conductive probe arm including proximal and distal portions, an electrode including a first end attached to said distal portion of said probe arm and a second unattached free end, and a mounting sleeve disposed on the probe arm; and
   b) a scope secured to the electrocautery probe by the mounting sleeve.

2. An electrocautery probe according to claim 1, wherein: said electrode comprises a loop electrode.

3. An electrocautery probe according to claim 1, wherein:
   said electrode extends from the probe arm at an angle, said electrode including a lower most portion, where the distance from said first attached end to said lowermost portion is less than the distance from said second free end to said lowermost portion.

4. An electrocautery probe according to claim 3, wherein:
   said distance from said first attached end to said lowermost portion is less than the distance from said second free end to said lowermost portion by approximately 0.10 inches.

5. An electrocautery probe according to claim 1, wherein:
   said electrode comprises a loop electrode and said free end includes one of a substantially pointed tip, and a substantially planar tip.

6. An electrocautery probe according to claim 5, wherein:
   said free end includes a substantially planar tip including a surface which is inclined.

7. An electrocautery probe according to claim 6, wherein: said surface has a sharp edge.

8. An electrocautery probe according to claim 1, wherein:
   said electrode is adapted to vaporize in substantially three orthogonal planes.

9. An electrocautery probe, comprising:
   a) exactly one conductive probe arm including proximal and distal portions;
   b) a mounting sleeve disposed on said probe arm;
   c) an axle coupled to a distal portion of said probe arm; and
   d) a roller bar electrode including a central bore, a first end, a second end, and a circumferential surface, said axle extending through said central bore and said first end being adjacent said distal portion of said probe arm, wherein said circumferential surface and said second end are each adapted to perform at least one of resection and coagulation.

10. An electrocautery probe according to claim 9, wherein:
    said second end includes a substantially pointed tip.

11. An electrocautery probe according to claim 9, wherein:
    said axle extends through said central bore beyond said second end and is adapted to perform at least one of tissue sculpting and spot coagulation.

12. An electrocautery probe according to claim 9, wherein:
    said axle comprises a bent distal portion of said probe arm.

13. An electrosurgical device, comprising:
    a) an electrocautery probe comprising exactly one conductive probe arm, a mounting sleeve disposed on the probe arm, and an electrode coupled to a distal portion of the probe arm, the electrode comprising a first end attached to the distal portion of the probe arm and a second unattached free end; and
    b) a scope mounted on the mounting sleeve relative to the electrocautery probe,
    wherein the electrode is aligned with a longitudinal axis of the scope for visualization of the electrode.

14. An electrosurgical device according to claim 13, wherein:
    said electrode includes a lateral midpoint, and a vertical plane extending through the longitudinal axis of the scope intersects said lateral midpoint.

15. An electrosurgical device according to claim 13 wherein:
    said electrode is situated in a substantially orthogonal manner to a vertical plane extending through the longitudinal axis of the scope.

16. An electrosurgical device according to claim 13, wherein:
    said electrode comprises one of a loop and a roller bar electrode.

17. An electrosurgical device according to claim 13, wherein:
    the electrode includes a lowermost portion located between the first attached end and the second free end, the lowermost portion being aligned with a vertical plane extending through the longitudinal axis of the scope.

18. An electrosurgical device according to claim 13, wherein:
    the probe arm is angled for alignment of the electrode with the longitudinal axis of the scope.

* * * * *